United States Patent [19]

Bundy

[11] Patent Number: 4,461,917
[45] Date of Patent: Jul. 24, 1984

[54] 9-DEOXY-9-METHYLENE-PGE COMPOUNDS

[75] Inventor: Gordon L. Bundy, Portage, Mich.

[73] Assignee: The Upjohn Company, Kalamazoo, Mich.

[21] Appl. No.: 832,329

[22] Filed: Sep. 12, 1977

Related U.S. Application Data

[60] Division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^3$ .......................................... C07C 177/00
[52] U.S. Cl. .................................................. 568/807
[58] Field of Search .................... 260/618 R; 568/807

[56] References Cited

U.S. PATENT DOCUMENTS 4,060,534 11/1977 Bundy ................................. 260/408

OTHER PUBLICATIONS

Samuelsson et al, Advances in Prostaglandin and Thromboxane Research, vol. 1 (1976) 488–491.

*Primary Examiner*—Bernard Helfin
*Attorney, Agent, or Firm*—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

1 Claim, No Drawings

9-DEOXY-9-METHYLENE-PGE COMPOUNDS

CROSS REFERENCE TO RELATED APPLICATIONS

The present application is a divisional application of Ser. No. 682,848, filed May 4, 1976, now issued as U.S. Pat. No. 4,060,534 on Nov. 29, 1977; which is a continuation-in-part of Ser. No. 651,622 filed Jan. 23, 1976, issued as U.S. Pat. No. 4,021,467 on May 3, 1977; which is a division of Ser. No. 556,768, filed Mar. 10, 1975, issued as U.S. Pat. No. 3,950,363 on Apr. 13, 1976.

The present invention relates to prostaglandin analogs, for which the essential material constituting disclosure therefor is incorporated by reference here from Ser. No. 682,848.

I claim:

1. A prostaglandin analog of the formula

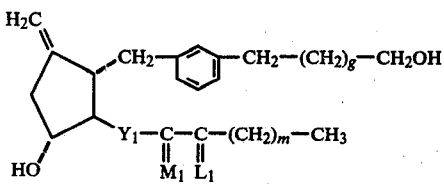

wherein $Y_1$ is trans—CH=CH—, —C≡C—, or —CH$_2$CH$_2$—;

wherein $M_1$ is

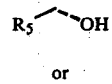

or

wherein $R_5$ is hydrogen or methyl;

wherein $L_1$ is

or a mixture of

wherein $R_3$ and $R_4$ are hydrogen, methyl, or fluoro, being the same or different, with the proviso that one of $R_3$ and $R_4$ is fluoro only when the other is hydrogen or fluoro;

wherein g is one, 2 or 3; and wherein m is one to 5, inclusive.

* * * * *